United States Patent
Lesage

(10) Patent No.: US 7,147,470 B2
(45) Date of Patent: Dec. 12, 2006

(54) DEVICE FOR CLEANING INTERDENTAL SPACES

(76) Inventor: Patrick Lesage, 9 Rue Constantine, Saint Malo (FR) F-35400

( * ) Notice: Subject to any disclaimer, the term of this patent is extended or adjusted under 35 U.S.C. 154(b) by 47 days.

(21) Appl. No.: 10/645,531

(22) Filed: Aug. 22, 2003

(65) Prior Publication Data

US 2004/0197735 A1      Oct. 7, 2004

(30) Foreign Application Priority Data

Apr. 7, 2003    (FR)    ................................... 03 04273

(51) Int. Cl.
*A61C 3/00*    (2006.01)
(52) U.S. Cl. ..................................... 433/141
(58) Field of Classification Search ................ 433/141, 433/216; 132/318, 321; 15/167.1; 401/103, 401/114
See application file for complete search history.

(56) References Cited

U.S. PATENT DOCUMENTS

| | | | | |
|---|---|---|---|---|
| 4,509,541 A | * | 4/1985 | Manciocchi, Jr. | ............ 132/322 |
| 4,922,936 A | * | 5/1990 | Buzzi et al. | ................. 132/321 |
| 5,868,149 A | * | 2/1999 | Yang | ........................... 132/328 |
| 6,050,818 A | | 4/2000 | Boland et al. | |
| 6,082,999 A | | 7/2000 | Tcherny et al. | |
| 6,418,940 B1 | * | 7/2002 | Tcherny et al. | ............. 132/321 |

\* cited by examiner

*Primary Examiner*—Melba Bumgarner
(74) *Attorney, Agent, or Firm*—Bacon & Thomas PLLC

(57) ABSTRACT

A device for cleaning interdental spaces has a tubular guide element having a first profiled open end to allow its positioning at the entry to an interdental space. A cleaning member mounted movably in the tubular guide element, fixed to a first end of a support member, the support member having a fixed longitudinal direction relative to the axis of the tubular guide element. A gripping member is provided for moving the cleaning member between a first position, in which they are entirely arranged inside the tubular element, and a second position, in which they are arranged entirely outside the first end of the tubular element.

7 Claims, 4 Drawing Sheets

DEVICE FOR CLEANING INTERDENTAL SPACES

BACKGROUND OF THE INVENTION

The subject of the invention is a device for cleaning interdental spaces.

The most well-known device for cleaning interdental spaces is generally called a brush. These cleaning means consist of a twisted metal core approximately 1 mm in diameter on which bristles defining a cylindrical or conical volume 5 to 10 mm in diameter are fixed.

They are often provided with a reasonably sophisticated handle to enhance their ergonomics. Because of its small size, this brush can effectively be inserted in the space between two adjacent teeth and efficiently clean that area.

However, these brushes have a number of drawbacks that either affect the cleaning efficiency or dissuade the user from continuing to use them.

These drawbacks will be explained with reference to the appended FIGS. 1A, 1B and 1C.

In FIG. 1C, a lower jaw 10 with teeth 12 and the lateral buccal wall 14 have been shown. This figure also shows a brush 16 with its bristles 18 and its gripping rod 20. The figure also shows the handle 20 of the brush being gripped by the fingers 22 of a first hand and the use of one or more fingers 24 of the other hand to move the buccal wall 14 away and to allow access to the desired interdental space 26.

FIG. 1A shows two consecutive teeth $12_1$ and $12_2$ and the corresponding interdental space 26. FIG. 1B shows the two teeth in section in the plane B—B.

Conventionally, to use the brush it is firstly necessary to place its end opposite the desired interdental space by holding back the soft tissue, such as the lip, cheek or tongue, and then the brush 16 is inserted in the axis of the interdental space and a back-and-forth movement is carried out.

Interdental spaces are usually located in the areas of the mouth that are difficult to access, particularly in the molar sector. Moreover, the lips and cheeks cannot be pushed back easily in order to allow comfortable positioning of the brush. Furthermore, the brushes include a core 20 consisting of a very fine twist of metal to allow insertion of the brush into the interdental space. The core of the brush can thus easily be deformed. Lastly, patients do not always have the skill required to present the end of the brush conveniently opposite the interdental space to be cleaned.

All the above considerations mean that the use of brushes of known type is therefore awkward, and the deformation of the brush gives rise to poor cleaning or early destruction of the equipment, and also to the frequent cessation of use of the cleaning device on the part of the user.

SUMMARY OF THE INVENTION

An object of the present invention is to provide a device for cleaning interdental spaces that is more efficient and easier to use than the current state of the art represented principally by interdental brushes.

To achieve this object according to the invention, the device for cleaning interdental spaces is noteworthy in that it comprises:

a tubular guide element having a first profiled open end to allow its positioning at the entry to an interdental space;

cleaning means (brush) mounted movably in said tubular element and having an axis constrained to remain coincident with that of said tubular element;

support means for the cleaning means having a fixed longitudinal direction relative to the axis of said tubular guide element; and gripping means for moving said cleaning means via said support means between a first position, in which they are entirely arranged inside said tubular element, and a second position, in which they are arranged entirely outside said first end of said tubular element.

Preferably, the device also comprises means for returning the cleaning means to their initial position and, also preferably, means for limiting the relative displacement of the support means and cleaning means relative to the tubular guide element.

It will be understood that when the interdental cleaning device is put into position the brush is entirely inside the tubular element. It therefore cannot be mechanically damaged. Moreover, this initial positioning is facilitated because the assembly consisting of the tubular element and the gripping means has sufficient mechanical strength to allow the soft tissue, such as the lip, cheek or tongue, to be moved away while bearing in the interdental space. Furthermore, the profiled open end of the tubular element considerably facilitates the initial positioning of the cleaning device at the entrance to the interdental zone.

According to a first embodiment, the gripping means comprise a tubular body with an axis aligned with that of said tubular guide element, the tubular body being movable relative to said tubular element in the common direction of their axes. The support means comprises a rod arranged along said common axis and has a first end integral with said means forming the brush and a second end integral with said tubular body.

It will be understood that, in this first embodiment, after the initial positioning of the cleaning device opposite the interdental space, by bearing on the tubular body the means forming the brush are made to emerge and automatically penetrate the desired interdental space.

According to a second embodiment of the invention, said gripping means comprise an elongate piece mounted movably in said tubular guide element and having a first end integral with the cleaning means.

In the case of this second embodiment of the invention, after the initial positioning of the device opposite the interdental space it suffices to bear on the gripping means in order to obtain the automatic emergence of the means forming the brush into the interdental space.

BRIEF DESCRIPTION OF THE DRAWINGS

Other characteristics and advantages of the invention will become more apparent upon reading the following description of a number of embodiments of the invention that are given by way of non-limiting examples. The description relates to the appended figures, in which.

DETAILED DESCRIPTION OF THE PREFERRED EMBODIMENTS

Figure 2:
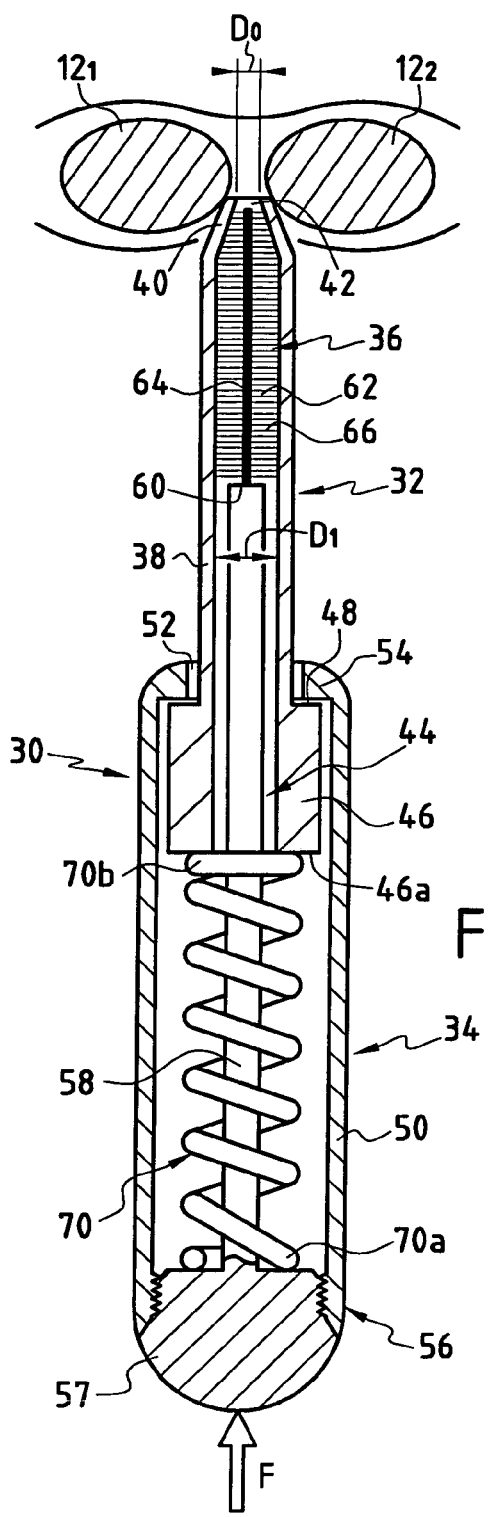
FIG. 2 is a view in longitudinal section of a first embodiment of the cleaning device.

With reference, firstly, to FIG. 2, a description will be given of a first embodiment of an interdental cleaning device 30. This device consists essentially of a tubular guide element 32, gripping means 34, cleaning means 36 forming a brush, and support means 58.

More precisely, the tubular guide element 32 includes a tubular piece 38 of which a first end 40 ends in a frustoconical shape for location and positioning in the interdental space 44. In its common part, the tubular piece 38 has an internal diameter D0, whereas its open end 42 has a diameter D1 less than D0. The second end 44 of the tubular piece 38 constitutes a widened part 46 that defines a shoulder 48 on its front face.

The gripping means 34 consist of a tubular body 50 with a first end 52 that is open to receive the tubular piece 38. The open end 52 includes an edge 54 that is able to cooperate with the shoulder 48 of the tubular piece. The second end 56 of the tubular body 50 is closed by a base 57. Mounted on this base 57 is an axial rod 58 forming the support means that extend over the entire length of the tubular body and penetrate the tubular piece 38. At its free end 60, the rod 58 is provided with a brush 62 of conventional type, which thus constitutes the cleaning means. The brush 62 includes a spindle 64 of very small diameter that is fixed to the end of the rod 58, and bristles 66 fixed on the spindle 64. The diameter of the brush is substantially equal to D0.

Preferably, the brush 62 is fixed to the end of the rod 58 by reversible fixing means 63, such as a screw-thread or bayonet system.

The cleaning device 30 further includes elastic return means consisting, in this embodiment, of a helical spring 70 surrounding part of the rod 58, a first end 70a of which bears on the base 57 of the tubular body and the second end 70b of which bears on the posterior face 46a of the widened part 46 of the tubular piece 38. At rest, i.e. in the position shown in FIG. 2, the spring 70 holds the shoulder 48 of the tubular piece on the edge 54 of the tubular body. In this position, the brush 62 is arranged entirely inside the tubular piece 38 and is thus protected.

Preferably, the base 57 is a piece distinct from the tubular piece 50 and is fixed by screwing or snap-fitting onto the end 56 of the tubular piece 50. This allows removal of the rod 58 and of the brush 62 in order to facilitate cleaning of the device.

It will be understood that if the user bears on the tubular body 50 in the direction of the arrow F, the end 42 of the device bearing on the teeth 12, the spring 70 is compressed and the brush 62 progressively emerges from the opening 42 of the tubular piece 38, thereby penetrating the interdental space 26.

It should be pointed out that the part 46 of larger diameter interacts with the inner face of the tubular body 50 in order to guide the tubular piece 38 in translation relative to the tubular body 50 and to maintain the alignment of the axes of the tubular body and of the tubular piece along the common axis X–X', which is, naturally, also the axis of the brush 62.

Figure 2A:
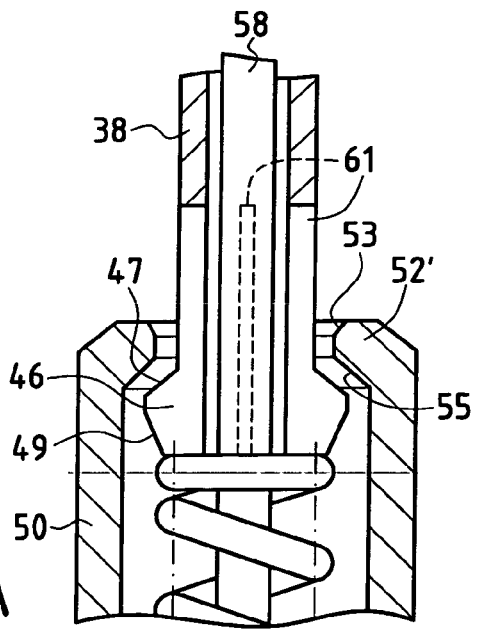

To facilitate assembly and dismantling of the device, it is also possible to give the end 46 of the tubular piece 38 and the end 52 of the tubular body 50 a special shape, shown in FIG. 2A.

The end of the tubular piece, which bears the reference 46', includes two chamfers 47 and 49 that are able to interact with the chamfers 53 and 55 provided on the end 52' of the tubular body 50. Moreover, the end of the tubular piece 38 may include longitudinal slots, for example four slots, such as 61, in order to facilitate elastic deformation of the piece during its assembly and dismantling by means of snapfitting.

Figure 1A:
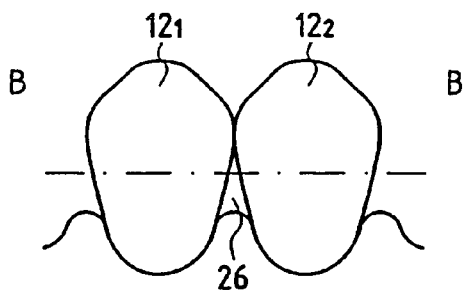
FIGS. 1A, 1B, and 1C already described illustrate the use of interdental brushes according to the state of the art.
Figure 1B:
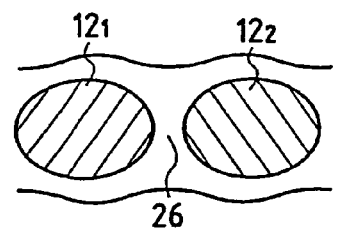
Figure 1C:
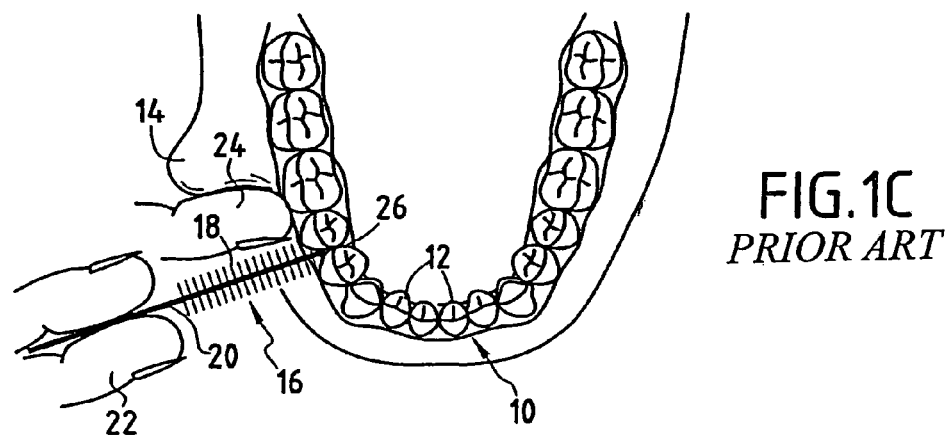
Figure 3A:
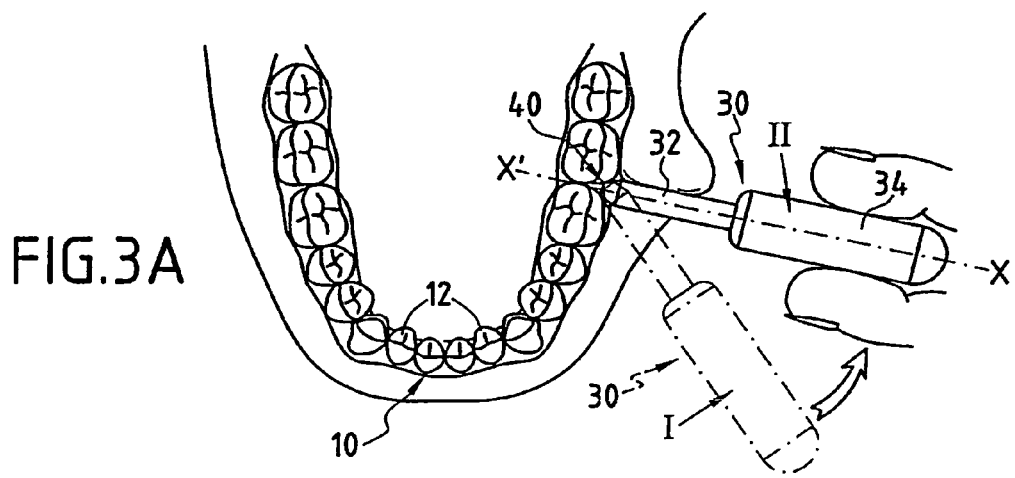
FIGS. 3A, 3B, and 3C illustrate the use of the first embodiment of the cleaning device.
Figure 3B:
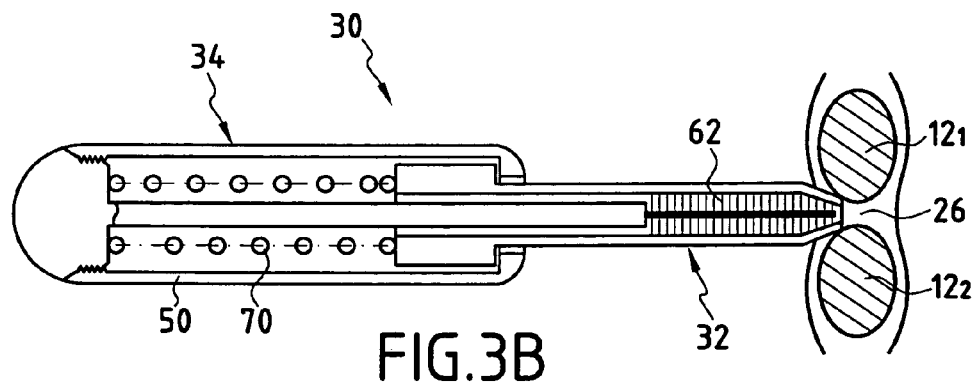
Figure 3C:
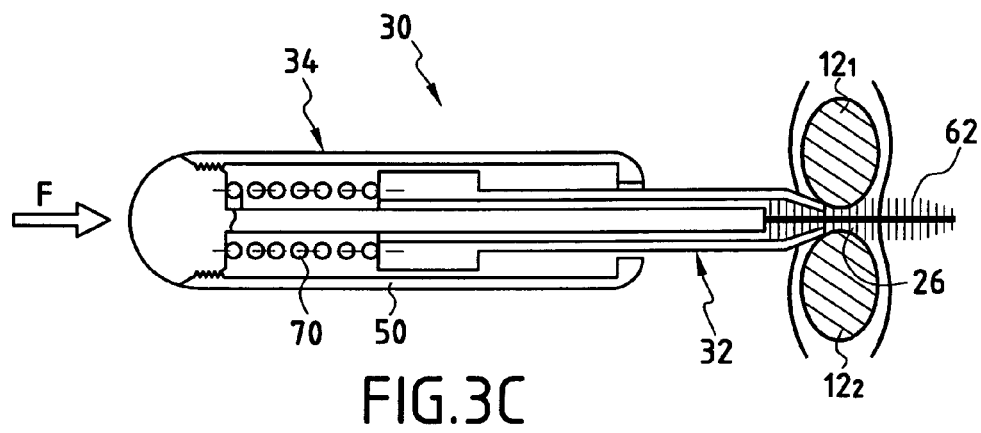

With reference, now, to FIGS. 3A through 3C, a description will be given of the use of this first embodiment of the cleaning device. FIG. 3A shows the initial position I of the cleaning device 30. In this position, the guide end 40 of the tubular element 32 bears on the end entry section of the interdental space. By pivoting, the user brings the device 30 into the position referenced II, simultaneously causing the cheek to move away. In this second position II, the axis X–X' of the device extends along the axis of the interdental space. In this initial position, as shown in FIG. 3B, the brush 62 is entirely included in the tubular element 32 and is thus mechanically protected.

In a second phase, shown in FIG. 3C, the user bears on the end 56 of the tubular gripping body 50. With the tubular element 32 being applied against the teeth, the spring 70 is compressed and the brush 62 emerges into the interdental space 26. To achieve convenient cleaning by means of a back-and-forth movement of the brush 62 in the interdental space, it suffices to press successively and then to slacken off pressure on the tubular gripping body 50.

Figure 4:
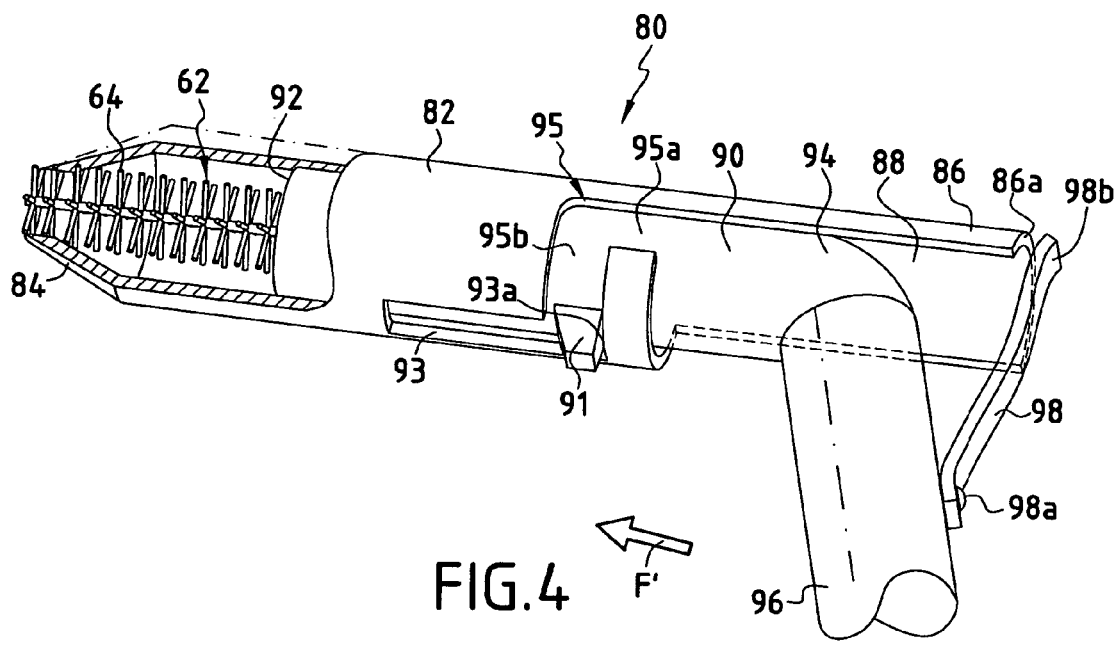
FIG. 4 shows, in axial section, a second embodiment of the cleaning device.

With reference, now, to FIG. 4, a description will be given of a second embodiment of the device for cleaning interdental spaces, which bears the reference 80. The device consists of a tubular element 82 with a first open end 84 that has a frustoconical shape and a second end 86 that is open and has a recess 88 close to this second end 86. Mounted slidably in the tubular piece 82 is a cylindrical piece 90 forming the support means, the first end 92 of which serves as a pusher for the brush 62. More precisely, the spindle 64 of the brush is fixed on the end 92 of the cylindrical piece 90. The second end 94 of the cylindrical piece 90 is extended by gripping means or handles 96 that emerge from the tubular piece 82 via the recess 88. The handle 96 is provided with an elastic leaf spring 98, a first end 98a of which is secured to the handle 96 and the second end 98b of which bears on the edge 86a of the end 86 of the tubular piece 82.

Through the effect of the leaf spring 98, the cylindrical piece 90 and therefore the brush 62 are held in a retracted position, as shown in FIG. 4. It will be understood that, as the tubular element 82 is bearing in the interdental space, the application of a force F' to the handle 96 of the device causes the piece 90 to slide in the tubular piece 82, which gives rise to the emergence of the brush 62 outside the end 84.

Figure 5A:
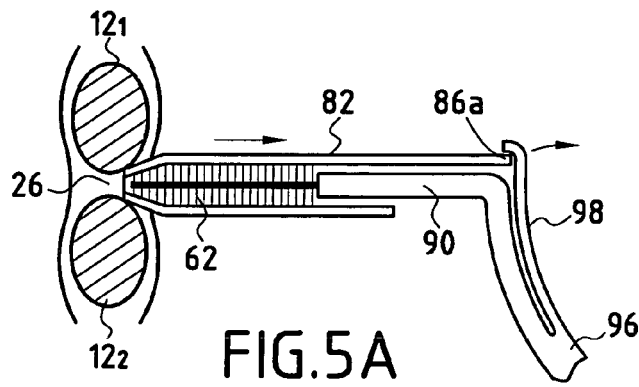
FIGS. 5A and 5B show the use of the cleaning device of FIG. 4.
Figure 5B:
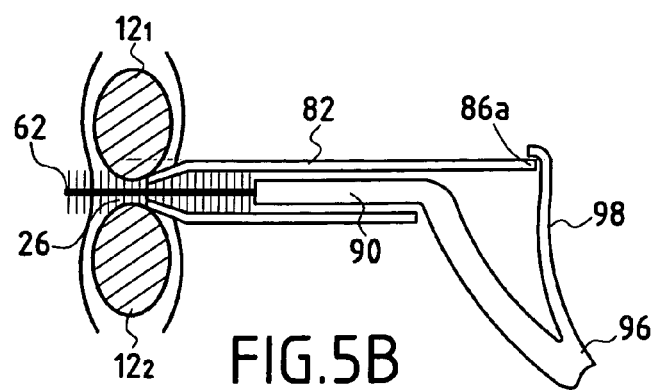

FIGS. 5A and 5B show the cleaning device 80 in its initial state and in its use state, respectively.

Figure 6:
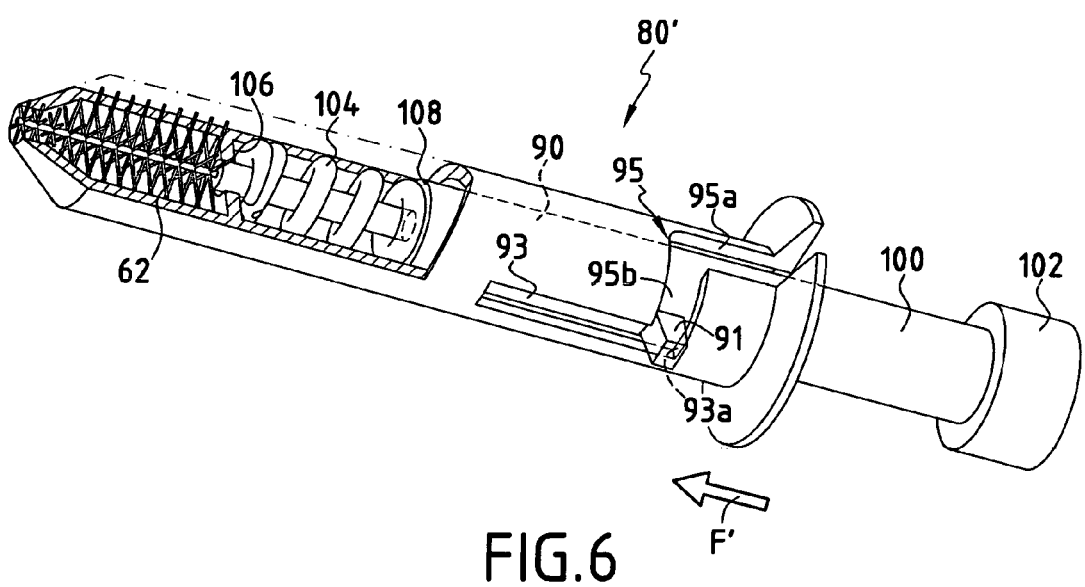
FIG. 6 shows, in longitudinal section, a third embodiment of the cleaning device.

FIG. 6 shows a variant 80' of the embodiment of FIG. 5. The difference lies essentially in that the gripping member 100 is in the extension of the cylindrical piece 90 and ends in an operating button 102. The elastic return means consist of a helical spring 104 surrounding a narrowed part of the piece 90 and mounted between a shoulder 106 inside the tubular piece 82 and the shoulder 108 of the cylindrical piece 90.

In order to simplify assembly and dismantling of the cylindrical piece 90 relative to the tubular piece 82, provision is preferably made in the latter two embodiments, in the tubular piece 82, for a bayonet-form slot 95 for the engagement of the stud 91. This slot includes a first portion 95a parallel to the slot 93 and opening out at the open end of the piece 82 and a second portion 95b in the form of an arc of a circle opening out in the slot 93.

It should be emphasized that, in all cases, the cleaning device is held in the retracted position by an elastic return system, and that this retracted position is defined by a mechanical stop constituting a means for limiting the relative displacement of the support means with regard to the tubular element.

What is claimed is:

1. A device for cleaning interdental spaces, comprising:
   a tubular guide element having an axis and a first profiled open end to allow its positioning at the entry to an interdental space and its bearing against teeth;
   cleaning means mounted movably in said tubular guide element and having an axis;
   support means for said cleaning means having a first end and a second end and a fixed longitudinal direction relative to the axis of said tubular guide element, said cleaning means being fixed at said first end of said support means and having an axis constrained to remain coincident with the axis of said tubular guide element;
   gripping means for moving said cleaning means comprising a tubular body having an axis aligned with the axis of said tubular guide element, said tubular body surrounding said tubular guide element and having an open first end for allowing the passage of said tubular guide element and a second end connected to the second end of said support means; and
   return means interposed between the second end of said tubular body and the second end of said tubular guide element;
   wherein when the first end of the tubular guide element is applied against teeth and a force is applied to said tubular body, the cleaning means move entirely outside the first end of said tubular guide element; and in the absence of force, the cleaning means are entirely disposed within said tubular guide element.

2. The cleaning device as claimed in claim 1, wherein said tubular body is movable relative to said tubular guide element along a common axis of said tubular body and said tubular guide element, and said support means comprise a rod arranged along said common axis and having a first end integral with said cleaning means and a second end integral with said tubular body.

3. The cleaning device as claimed in claim 2, wherein said return means is a helical spring surrounding said rod and interposed between said tubular guide element and said tubular gripping body.

4. The cleaning device as claimed in claim 1, wherein said cleaning means comprise an interdental brush.

5. The cleaning device as claimed in claim 4, wherein the internal diameter of a common part of said tubular guide element is substantially equal to the external diameter of said brush, and wherein the internal diameter of the first end of the tubular guide element is smaller than that of the common part of the tubular guide element.

6. The cleaning device as claimed in claim 1, wherein said first profiled end of the tubular guide element is frustoconical in order to facilitate the positioning of said device relative to the interdental space.

7. The device as claimed in claim 1, further comprising fixing means disposed at the first end of said support means for removably fixing said cleaning means with said support means.

* * * * *